US009017346B2

(12) United States Patent
Kia et al.

(10) Patent No.: US 9,017,346 B2
(45) Date of Patent: Apr. 28, 2015

(54) AUTOMATED SUTURE DEVICE

(71) Applicant: MSK, LLC, Flint, MI (US)

(72) Inventors: Michael Kia, Grand Blanc, MI (US); Mehrdad Zadeh, Grand Blanc, MI (US)

(73) Assignee: MSK, LLC, Flint, MI (US)

( * ) Notice: Subject to any disclaimer, the term of this patent is extended or adjusted under 35 U.S.C. 154(b) by 0 days.

(21) Appl. No.: 13/714,540

(22) Filed: Dec. 14, 2012

(65) Prior Publication Data

US 2013/0158568 A1    Jun. 20, 2013

Related U.S. Application Data

(60) Provisional application No. 61/570,371, filed on Dec. 14, 2011.

(51) Int. Cl.
*A61B 17/04* (2006.01)
*A61B 17/06* (2006.01)

(52) U.S. Cl.
CPC ......... *A61B 17/0469* (2013.01); *A61B 17/0467* (2013.01); *A61B 17/0482* (2013.01); *A61B 17/06166* (2013.01); *A61B 2017/06104* (2013.01); *A61B 2017/0619* (2013.01)

(58) Field of Classification Search
USPC ........... 606/144, 27, 228, 145, 146, 147, 139, 606/148, 142, 143, 151, 181–183, 153, 155, 606/157, 158, 221, 219
See application file for complete search history.

(56) References Cited

U.S. PATENT DOCUMENTS

| | | | |
|---|---|---|---|
| 4,509,517 A * | 4/1985 | Zibelin | 606/127 |
| 5,417,700 A | 5/1995 | Egan | |
| 5,562,686 A * | 10/1996 | Sauer et al. | 606/144 |
| 5,797,927 A * | 8/1998 | Yoon | 606/144 |
| 5,860,992 A | 1/1999 | Daniel et al. | |
| 2002/0116010 A1 | 8/2002 | Chung et al. | |
| 2004/0092969 A1 | 5/2004 | Kumar | |
| 2005/0049638 A1 | 3/2005 | Mandelbaum | |
| 2008/0172071 A1 | 7/2008 | Barker | |
| 2009/0182353 A1* | 7/2009 | Snell et al. | 606/144 |
| 2011/0196388 A1* | 8/2011 | Thielen et al. | 606/144 |
| 2013/0158568 A1 | 6/2013 | Kia et al. | |

* cited by examiner

*Primary Examiner* — Jocelin Tanner
(74) *Attorney, Agent, or Firm* — Harness, Dickey & Pierce, PLC

(57) ABSTRACT

A suture device including a hollow shaft; a pair of jaws disposed at an end of the hollow shaft, at least one of the jaws being actuated by an actuation arm coupled to an actuation mechanism, and each of the jaws including a channel formed therein for carrying a suture; a locking device disposed in the hollow shaft operable to grip an end of the suture; a cutting device disposed in the hollow shaft operable to cut an opposing end of the suture; and a heating device configured to remove the suture from the channels of the pair of jaws, and fuse the suture. The suture can include a core surrounded by an outer coating, wherein the outer coating has a melting point less than a melting point of the inner core.

12 Claims, 10 Drawing Sheets

AUTOMATED SUTURE DEVICE

CROSS-REFERENCE TO RELATED APPLICATIONS

This application claims the benefit of U.S. Provisional Application No. 61/570,371, filed on Dec. 14, 2011. The entire disclosure of the above application is incorporated herein by reference.

FIELD

The present disclosure relates to devices and methods of securing a suture around a vessel or ductal structure, as well as to devices and methods of securing mesh laproscopically.

BACKGROUND

This section provides background information related to the present disclosure which is not necessarily prior art.

Unlike traditional open surgery where tasks such as ligating vessels or tying off ductal structures are performed with ease, these same tasks in laparoscopic surgery are much more difficult. In traditional open surgery, these tasks are performed by the surgeon using varied types of suture material and manually passing the suture around the structure and then manually tightening to occlusion using multiple knots. Alternatively, the surgeon may consider clamping the structure first on either side, dividing it, and then manually tying each side of the vessel or ductal structure.

Varied mechanisms exist for the ligation of vascular or ductal structures in laparoscopic surgery. The first includes metallic or plastic clip mechanisms. These can be somewhat secure, but are limited by size and length of intended structure. Metallic clip mechanism have the advantage of multiple clips per device, but are generally limited to structures of one centimeter in diameter and have a tendency to slide on vascular tissue. Plastic clip systems can come in slightly larger sizes, but are typically single-load devices and have a tendency to misalign. They tend to be slightly more secure than metallic.

The second type of device commonly available is a linear-stapling device that uses multiple rows of small staples to secure and divide tissue. The advantages of these devices are the large amount of tissue that can be ligated as well as the ability to divide all types of tissues. The staples are considered very secure. However, the devices currently are quite bulky and have a large end effector that can require a larger cannula as well. The end effector size requires adequate space to encompass the vessel or ductal structure which can, in certain areas of the body, be very difficult due to the close proximity of abdominal cavity or of other vessels.

Finally, the most recent type of sealant devices utilized are varied types of energy including ultrasonic or bipolar electricity to denature proteins to seal structures. These devices can be very rapid in use and allow for continuous usage, they are limited in the size of vessel and type of tissue that can be ligated with adequate seal. Currently recommendations are for structures less than approximately 7 mm.

Mechanical devices designed to place a preformed loop around vessel structures do exist. However these types of devices are limited by the need for an open end of the intended tissue to be available to place the suture around.

Some automated devices that have been created for suturing tissue that may be utilized for the purpose of ligating a vascular structure. U.S. Pat. No. 5,417,700 describes a device specific to using a needle to penetrate tissue for the purpose of approximating tissue and then utilizes energy to seal the suture. This device's primary intention is for the approximation of tissue and is limited in its size of vasculature ligation as well as the presence of a needle to advance the suture material which can penetrate vasculature structures causing damage. The device additionally describes the ability to utilize heat to fuse suture. However, the use of an endplate to overlap the suture can result in an unwanted space in the loop of suture resulting in incomplete occlusion.

In other minimally invasive surgical procedures, small incisions are made in the abdomen and specialized instruments are used through varied access points to accomplish the performance of a surgical procedure. Unlike traditional open surgery involving a large incision, technical aspects such as suturing and tying are much more difficult.

In traditional open surgery, a commonly-used device is suture on a curved needle used for suturing and subsequently manually tying. In contrast, the use of a curved needle in laparoscopic surgery is especially difficult and rarely performed in the same manner, or speed as in open surgery. Additionally, certain angulations that occur during laparoscopic surgery, such as sewing against the anterior abdominal wall are even more difficult.

A common procedure that requires sewing against the abdominal wall is the performance of ventral or incisional abdominal wall hernia repairs. During open surgery, a synthetic or biological mesh is sewn with suture on a curved needle onto the abdominal wall to affix the mesh to the abdominal wall. The depth of penetration is critical to obtaining adequate layers of the abdominal wall. In laparoscopic surgery due to the severe technical difficulty of suturing the abdominal wall, the technique of mesh fixation has had to be altered to accommodate the inability for most surgeons to replicate the technique used in open surgery.

Typically during laparoscopic ventral hernia repair a flat piece of synthetic mesh is rolled and inserted through small opening into the insufflated abdominal cavity. There it is unrolled and affixed to the abdominal wall using a tacking device with or without the addition of sutures. The tacking devices are varied in their delivery system but fall into two categories, non-absorbable metal tacks and absorbable polymer tacks. While efficient in its use the tacks are limited in utility. Non-absorbable tacks are titanium and expose the bowel to bare metal which has shown the risk of injury to the intestine. Absorbable tacks are made from polymers and therefore are limited in their gripping strength and depth of penetration.

As solely tacking the mesh to the abdominal wall may not provide adequate apposition to limit the mesh migration, the same types of sutures used in open surgery are typically used as adjunct. However in laparoscopic surgery the sutures are passed through the abdominal wall from an external source into the abdomen then pulled back out and tied down, so called trans-fascial suturing. While very secure, this technique is difficult and time consuming and exposes the patient to the risk of transmigration of bacteria from the skin surface. The ideal solution would be to replicate the same technique used in open surgery of utilizing a curved needle and suture during laparoscopic surgery.

SUMMARY

This section provides a general summary of the disclosure, and is not a comprehensive disclosure of its full scope or all of its features.

With respect to a ligation suturing device, an object of the present disclosure is to provide a device that can advance a strand of suture material circumferentially around a vessel or tubular tissue, retract, and tighten the suture, and effectively seal the suture and cut it in a reliable repeatable manner.

It is another object of the present disclosure to complete the performed tasks with one device that can be operated by one hand. The advancement of the suture, retraction, and seal will be automated to minimize error.

Is a further object of the present disclosure that the device is capable of securing tissue of varied sizes without changing of the end effector. The device will have the capacity to completely encircle the tissue while intact with minimal dissection. This provides the advantage of working in areas with limited space, as well as ensuring that the intended structure is completely included in the intended suture.

It is a yet another object of the present disclosure that the device will have sensor technology to allow for proper repeatable operation in the varied conditions and potential obstructive effects of different areas of the human body. The device shall have feedback for such events to the operating surgeon.

It is further object of the present disclosure that the suture is tied without the formation of a knot or metallic or plastic clamping mechanism. It is a further object of the present disclosure that the suture used is a biocompatible polymer designed to have a low thermal melting temperature. This will allow the heat source used for sealing to be in proximity to live tissue without injury.

It is a further object of the present disclosure that the polymeric strand has an outer layer and an inner core that are of differing thermal temperatures to allow for melting and fusion of the outer layer while permitting continued tension maintained by the inner core.

It is yet another object of the present disclosure to provide an instrument well suited to perform its described tasks in areas of limited access (i.e., arthroscopic, laparoscopic or endoscopic procedures).

Yet another object of the present disclosure is to provide a device that can replicate the standard of securing a mesh to the abdominal wall as seen in open surgery. The device would be able to use a hallow cored curved needle to pass through the mesh and tissue, then advance a suture through the hollow core, tighten the suture out of the needle, and effectively seal and secure the loop without the use of a knot. This would be done in a reproducible manner without extraction of the device.

It is an object of this invention to have a device with a curved needle as the end-effector that is hollow, but has an opening for suture to be withdrawn out of it. The needle will rotate through tissue and the suture will be advanced into the hollow core then be pulled out of the needle after completion of the loop during tightening.

It is another object of this invention to complete the performed tasks with one device that can be operated by one hand. The advancement of the suture, retraction, and seal will be automated to minimize error.

It is a yet another object of this device that the device will have sensor technology to allow for proper repeatable operation in the varied conditions and potential obstructive effects of different areas of the human body. The device shall have feedback for such events to the operating surgeon or to the device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
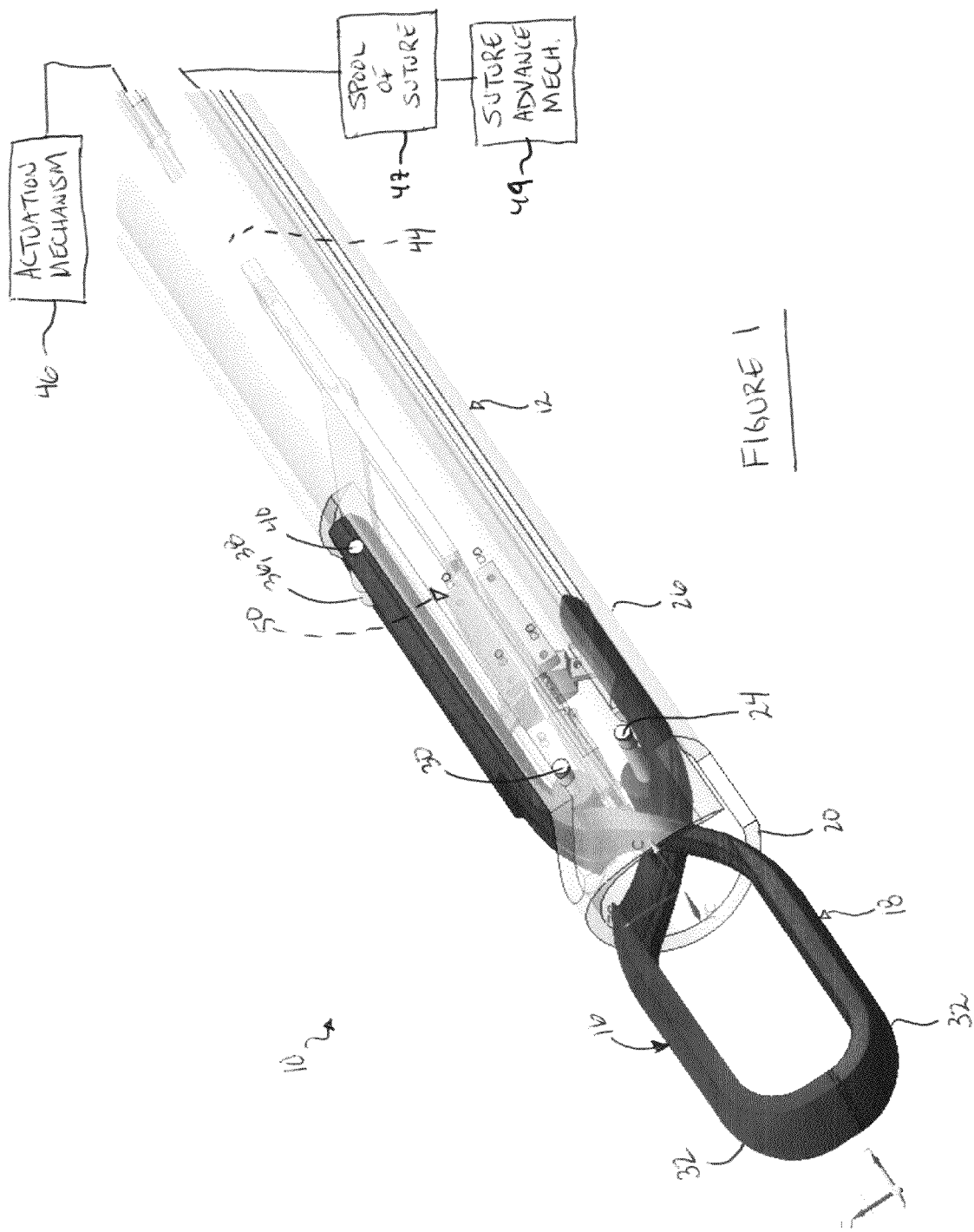
FIG. 1 is a perspective view of a suture device according to a principle of the present disclosure.

Example embodiments will now be described more fully with reference to the accompanying drawings.

The foregoing objects are met in a suturing device and process. This device utilizes in a preferred embodiment a channeled device wherein a suture is advanced through an end effector that creates a closed loop. The suture is secured within the device at its distal end and then retracted from its proximal end.

In a preferred embodiment the device comprises an actuation mechanism such as a movable handle that cooperates with mechanical components in the handle attached to a shaft. The handle will have a manually operated clamping mechanism for approximation of the end effector. The device can also have a locking and unlocking mechanism. The handle will also have handle mechanisms for advancement and retraction of the suture. Additionally, handle mechanisms will be available for actuating sealing the suture. A single trigger or multiple trigger system will be available.

In another preferred embodiment the handle will contain a spool of suture controlled by a rotary mechanism. The mechanism by itself or in conjunction with other components will serve for advancement and withdrawal of the suture down the shaft. The mechanism may have a sensor that measure torque, resistance or tension or a combination of said. The suture shall pass down a channel in the shaft toward the end effector.

The shaft will contain one to multiple channels and mechanical components. The channels will carry suture. The mechanical components will include a mechanism for rotating the curved needle. Additional mechanical components may be included to achieve the desired properties of the device.

In a preferred embodiment, the shaft will have contained in it a clamping mechanism capable of holding one end of suture. The clamp may also be located in the handle of the device. The clamp may be electrically or mechanically controlled or be of a piezoelectric or electromagnetic type.

In a preferred embodiment, the shaft will have contained in it a cutting mechanism capable of cutting one end of suture. The cutting mechanism may be on the same control rod of the clamping mechanism.

In a preferred embodiment the end effector is of a curved needle. The end effector can vary in size and may be offered in different sizes. It contains a grooved channel in continuity with the previous shaft. The grooved channel may be shaped to not allow the suture to be withdrawn without internal tension. Likewise the channel may be covered with a rubber or polymer flap to allow for coverage of the suture during passing while providing for release as the suture retracts.

In a preferred embodiment the heating element may be capable of advancement from the shaft to reduce the distance of the approximation of the loop from the tissue.

In a preferred embodiment the suture shall consist of a dual system with an inner core and outer core. The inner core may be of a material with a high melting temperature such as but not limited to polymer, suture, or wire. The outer core shall be of a material of a lower melting temperature.

Figure 2:
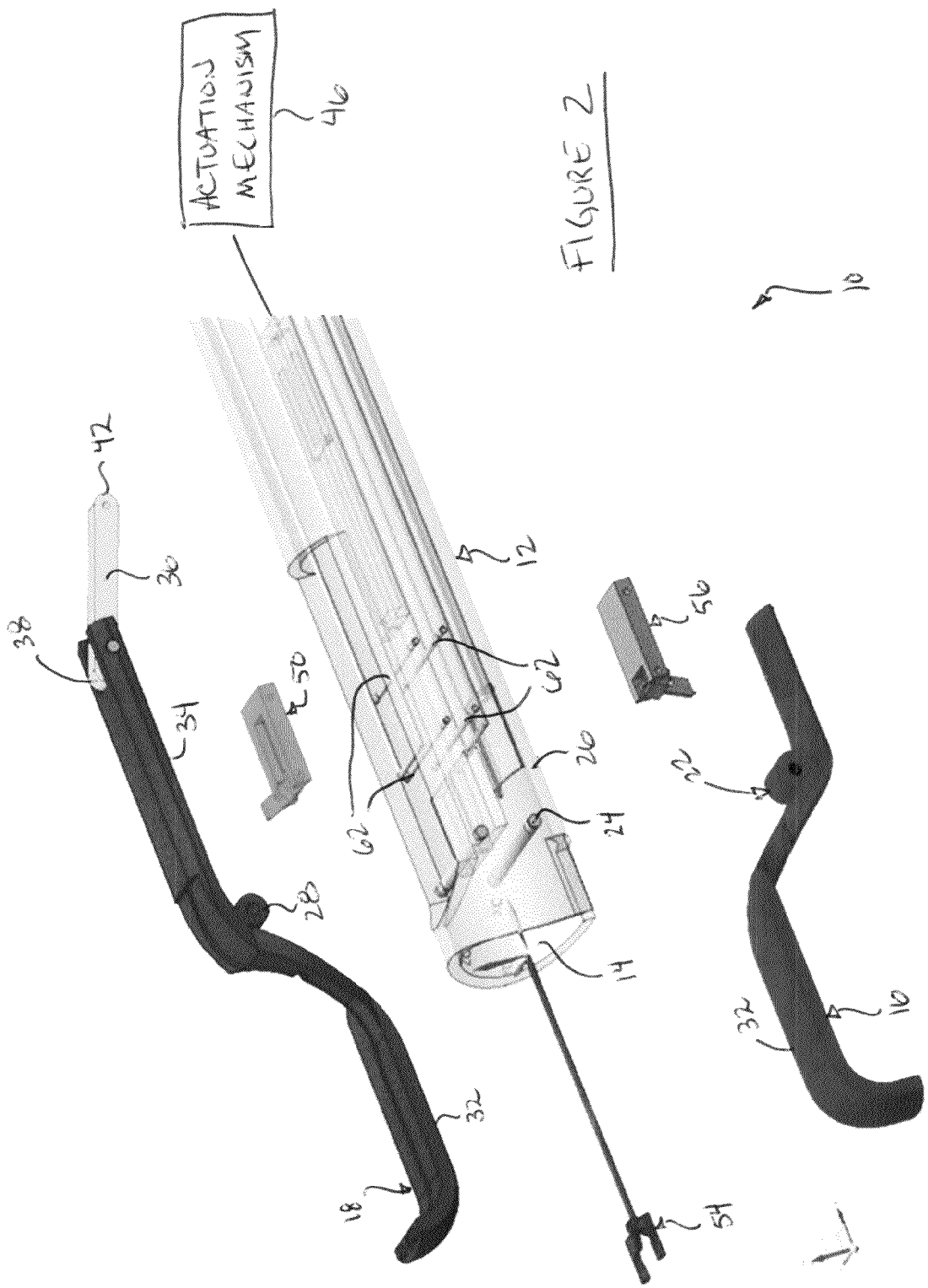
FIG. 2 is an exploded perspective view of the suture device illustrated in FIG. 1.

FIGS. 1-10 illustrate a suture device 10 in accordance with a principle of the present disclosure. As best shown in FIGS. 1 and 2, suture device 10 includes an elongated housing or shaft 12. Shaft 12 may be cylindrical in shape having a hollow interior 14. Within interior 14 may be disposed various mechanisms, as will be described in greater detail below, for advancing a suture material around a vessel, securing the suture around the vessel, and mechanically actuating a pair of jaws 16 and 18 disposed at a distal end 20 of shaft 12. A first or lower jaw 16 is generally immovable or fixed to shaft 12. A second or upper jaw 18 is movable relative to shaft 12 as well as relative lower jaw 16. To fix lower jaw 16 to shaft 12, lower jaw 16 can include a cylindrically-shaped aperture 22 that receives a first pin 24 through an exterior 26 of shaft 12. Upper jaw 18 also includes a cylindrically-shaped aperture 28 receives a second pin 30 through exterior 26 of shaft 12.

Each jaw 16 and 18 is shaped to encircle a vessel to be ligated. In this regard, each jaw 16 and 18 includes a calipered end 32. Top jaw 18 also includes an actuation end 34 that is coupled to a cam or actuation arm 36. Actuation arm 36 includes a first end 38 that is pivotably coupled to actuation end 34 of top jaw 18 via a pin 40. A second end 42 of actuation arm 36 is coupled to a wire 44 that is mechanically actuated by an actuation mechanism 46 that pushes and pulls wire 44. As wire 44 is pushed and pulled by actuation mechanism 46, actuation arm 36 forces top jaw 18 to pivot about second pin 30 to open and close top jaw 18 relative to lower jaw 16.

Figure 3:
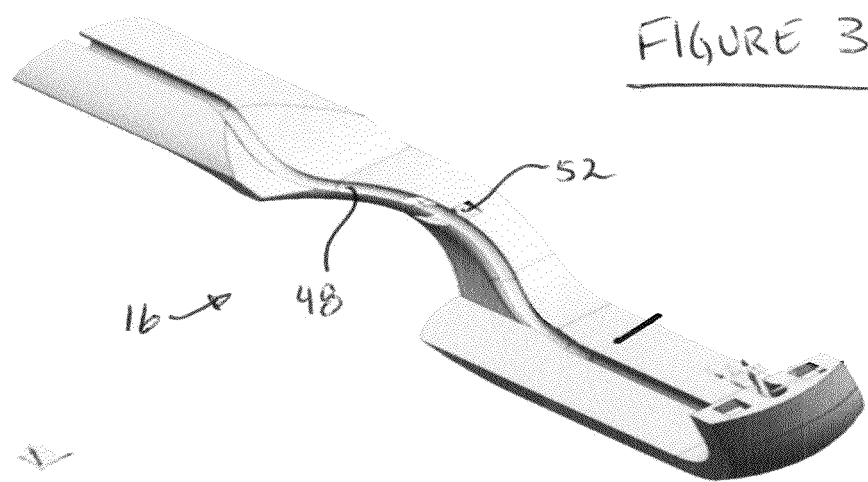
FIGS. 3 and 4 are perspective views of upper and lower jaws of the suture device illustrated in FIG. 1.
Figure 4:
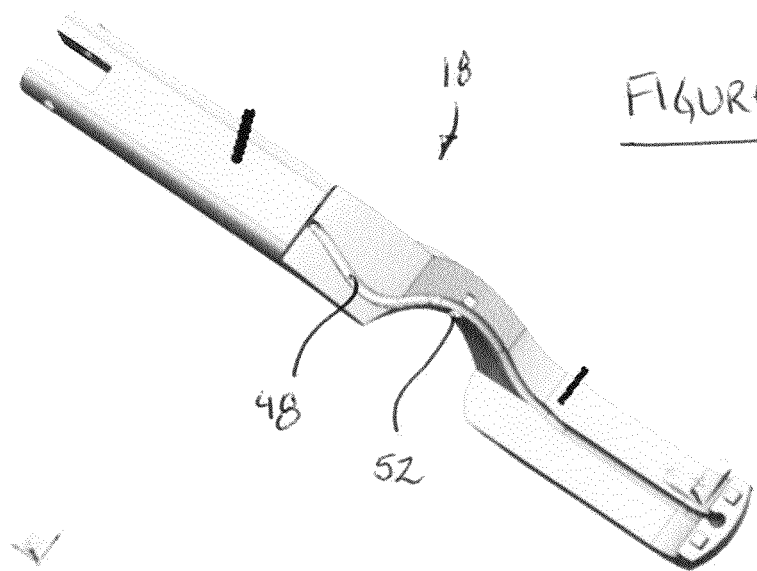
Figure 5:
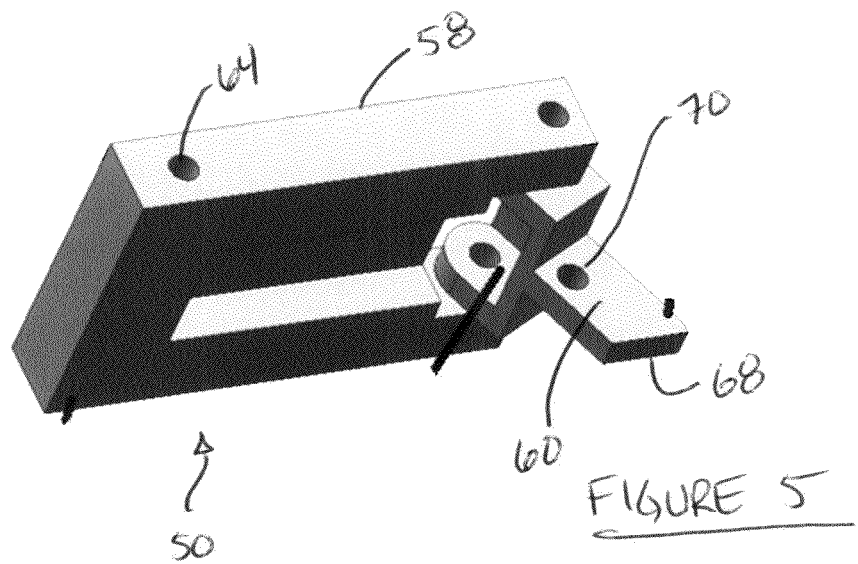
FIG. 5 is a perspective view of a locking device illustrated in FIG. 2.

As best shown in FIGS. 3 and 4, each of lower jaw 16 and upper jaw 18 include a channel 48 for receiving the suture material and allowing the suture material to pass over the vessel or tissue to be ligated. Suture material may be held on a spool 47 and fed and pulled tight when jaws 16 and 18 are closed by a suture advance device 49 that is mechanically or electrically actuated. In particular, after upper jaw 18 has been opened and closed around the vessel or tissue to be ligated, the suture material can be advanced through lower jaw 16 to loop over the vessel to be ligated and into the channel 48 formed in upper jaw 18. The suture will then travel through the channel 48 of the upper jaw 18 back into the interior 14 of shaft 12. Once the suture has travelled back into the interior 14 of shaft 12, the suture may be gripped by a locking device 50. Each of lower jaw 16 and upper jaw 18 include a rectangular-shaped slot 52. Slot 52 allows passage of a movable heating element 54 that is designed to cross opposing ends of the suture and, once the opposing ends of the suture are crossed, fuse the opposing ends of the suture together to complete ligation of the vessel or tissue to be ligated. Description of heating element 54 and operation thereof will be described in greater detail later.

Suture device 10 includes locking device 50 to lock the suture in place during the fusing of opposing ends thereof. After the opposing ends of the suture have been fused, a cutting device 56 may be used to cut the suture. Each of locking device 50 and cutting device 56 include a mounting structure 58 and a movable peg 60. Each peg 60 is pivotable relative to mounting structure 58. Similar to jaws 16 and 18, each mounting structure 58 may be fixed to shaft 12 by pins 62 that pass through apertures 64 formed in each mounting structure 58. Pegs 60 of locking device 50 and cutting device 56 differ in that cutting device 56 includes a blade 66 formed at an end thereof, while locking device includes a gripping surface 68. Gripping surface 68 includes a high frictional surface that is operable to grip the suture. To make gripping surface 68 be frictional, gripping surface 68 may be roughened or be formed of a different material than peg 60.

To actuate each peg 60 of locking device 50 and cutting device 56, each peg includes a through-hole 70 that is secured to an independently controlled shape-metal alloy wire 72. Shape-metal allow wires 72 are formed of alloys that have two crystalline phases, Austenite (high-temperature phase) and Martensite (low temperature phase). Upon application of a voltage to the wires 72, the wires may heat up, which can deform the wires 72 to pull pegs 60 to positions that will engage the suture to either cut or grip the suture. To allow pegs 60 to engage the suture when appropriate, each of lower and upper jaw 16 and 18 include an elongated slot 73 that allows for passage of pegs 60. When application of the voltage ceases, the wires 72 will return to their original shapes and actuate the push pegs 60 away from engagement with the sutures. To assist in pushing pegs 60 away from the suture during non-application of voltage to the wires 72, each peg 60 can also include a spring (not shown) that assists in reverting the peg 60 back to an un-engaged position away from the suture.

Figure 6:
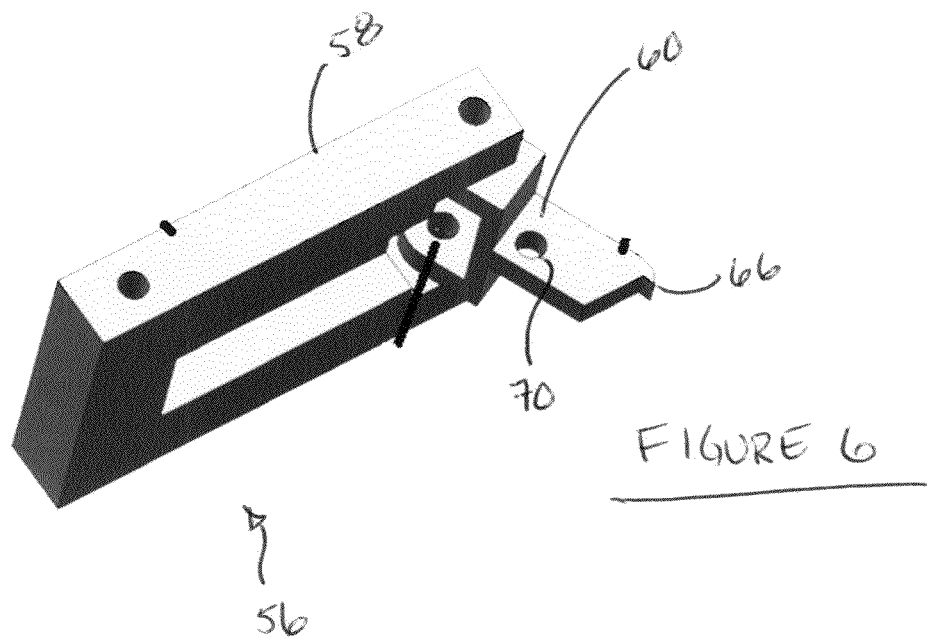
FIG. 6 is a perspective view of a cutting device illustrated in FIG. 2.
Figure 7:
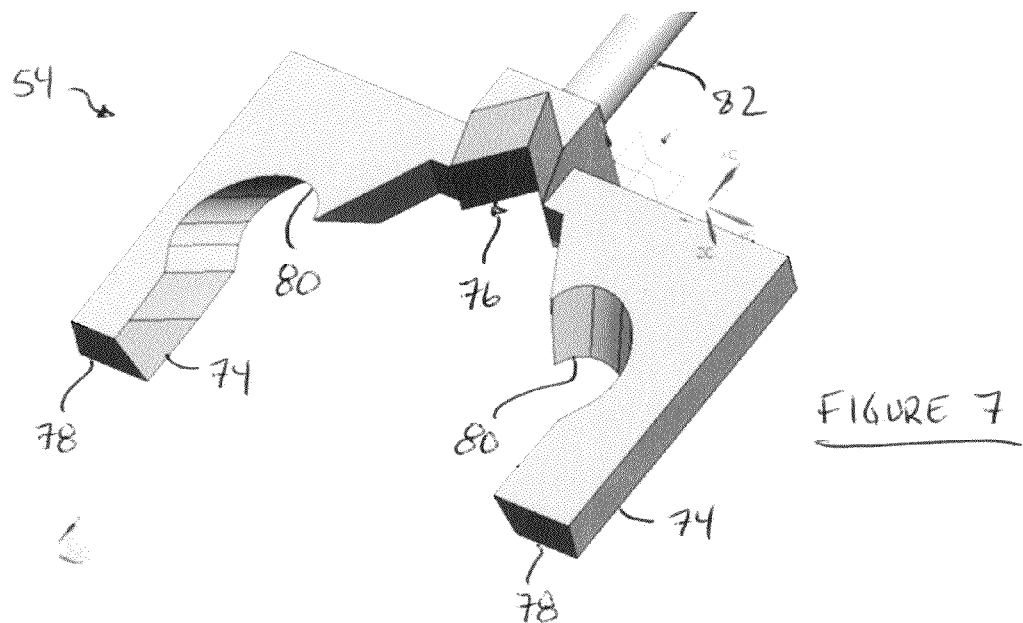
FIG. 7 is a perspective view of a heating device according to a principle of the present disclosure.
Figure 8:
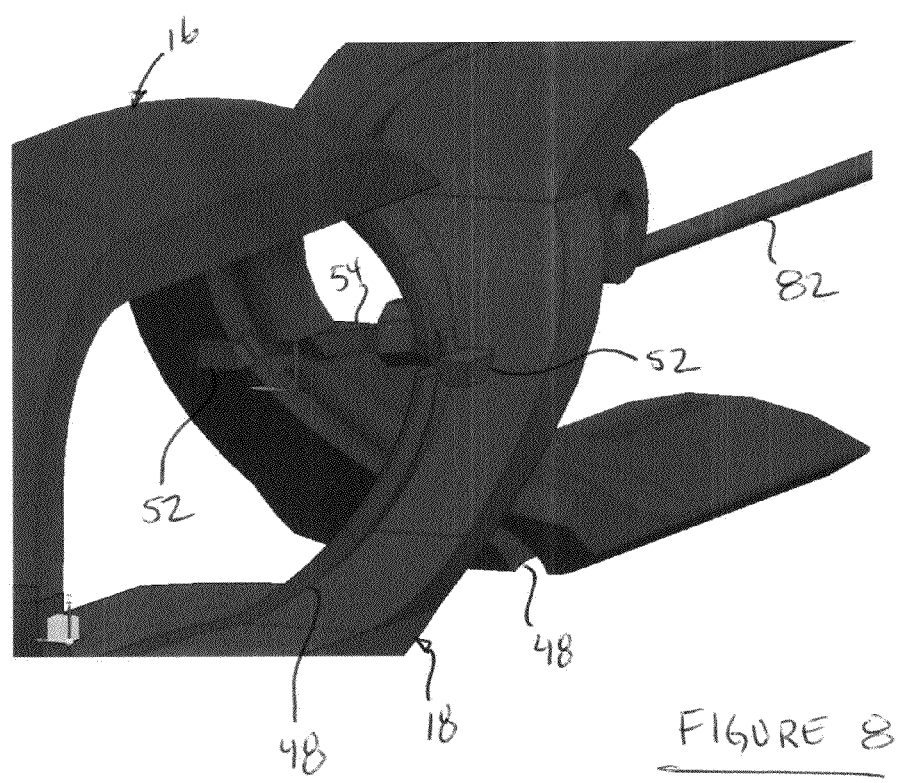
FIG. 8 is a perspective view of the heating device passing through slots formed in jaws of the suture device.
Figure 9:
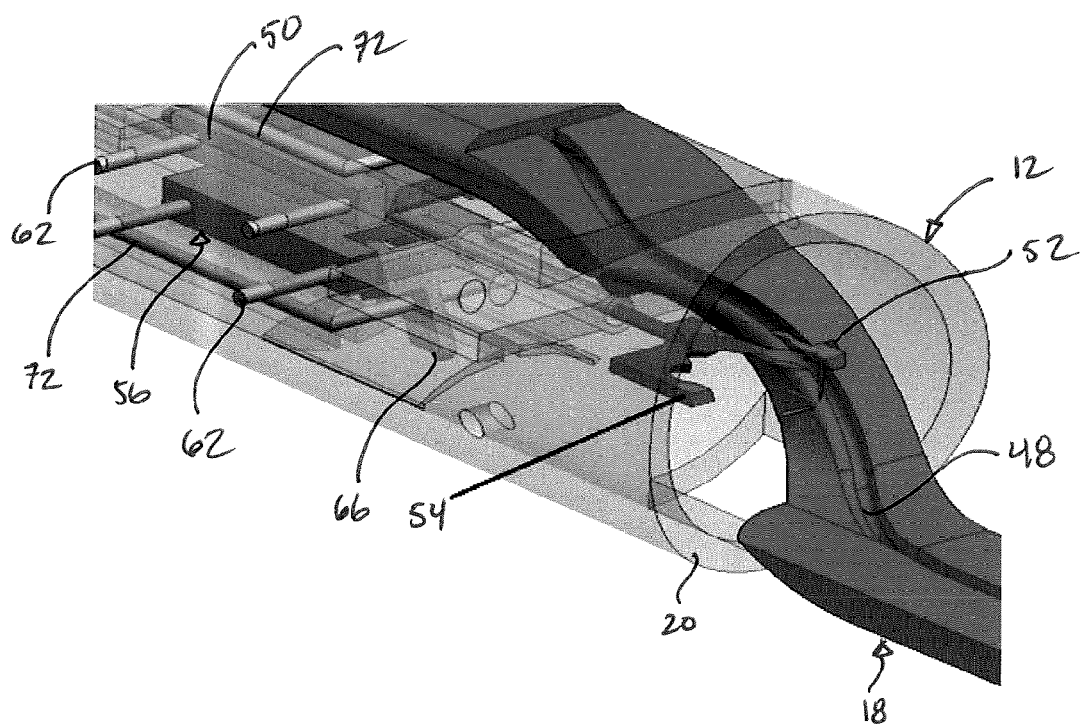
FIGS. 9 and 10 are perspective view of the suture device, with a lower jaw thereof removed.
Figure 10:
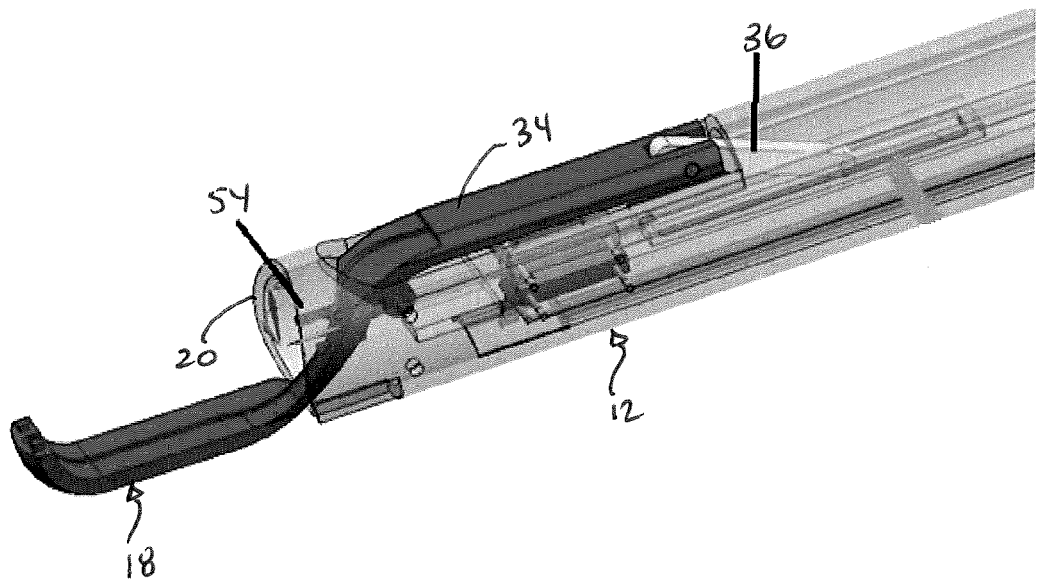

Once the suture has been gripped by locking device 50, and before the suture is cut by cutting device 56, the opposing ends of the suture need to be fused. To fuse the opposing ends of the suture together, ligation device includes heating element 54. As best shown in FIGS. 7-9, heating element 54 may be a substantially planar device including a pair of guiding elements or wings 74. Each wing 74 is designed and configured to be moved through slots 52 formed in lower and upper jaws 16 and 18 (FIG. 6). Each wing 74 meets at a seat 76 of heating element 54 where opposing ends of the suture can be crossed over one another and, upon application of a voltage to heating element 54, can be fused together through resistance heating.

Between seat 76 and distal ends 78 of heating element 54 are formed U-shaped recesses 80. U-shaped recesses 80 are shaped and designed to correspond to channels 48 formed in each of lower jaw 16 and upper jaw 18. As heating element 54 is moved forward through actuation by heating rod 82 through slots 52, U-shaped recesses 80 catch opposing ends of the suture and force the suture towards seat 76. Once suture is fused at seat 76, heating element 54 can be retracted through slots 52, while cutting device is actuated to cut the suture. Locking device 50 can then be disengaged from the opposing end of the suture. Then, upper jaw 18 can be actuated by actuation arm 36 to allow ligation device 10 to be removed from the location about the vessel that has been ligated.

Figure 11:
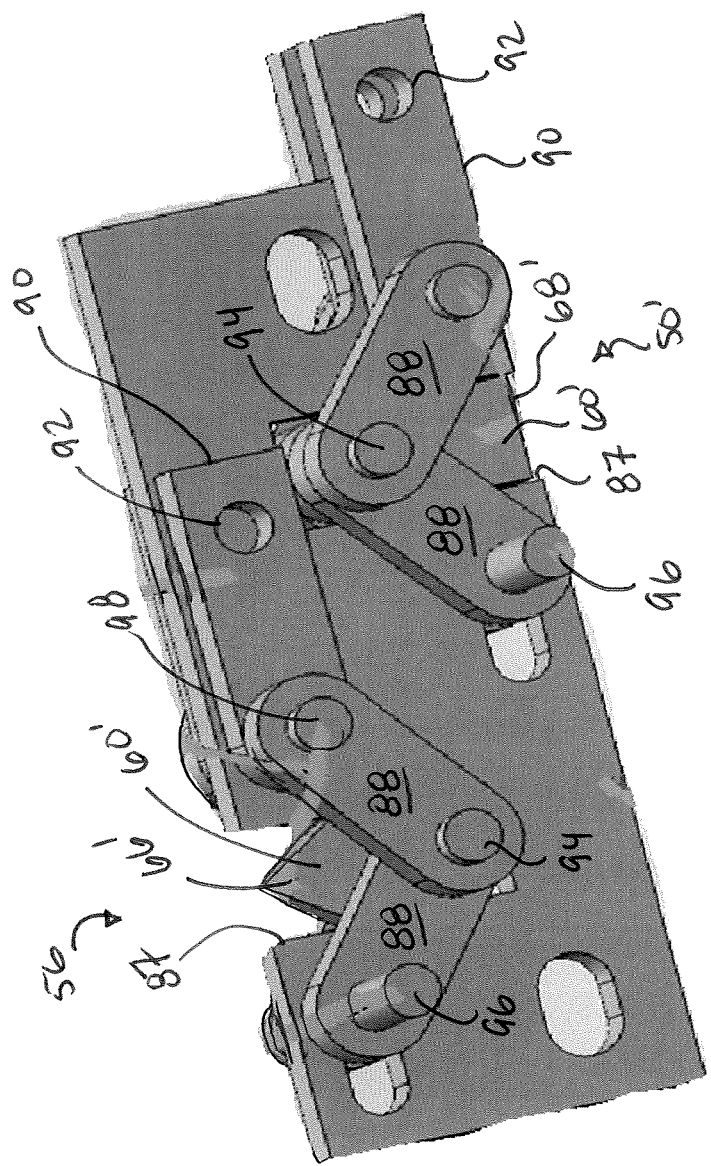
FIG. 11 is a perspective view of an integrated cutting and locking device according to a principle of the present disclosure.

As described above, the locking and cutting devices 50 and 56 are separately formed devices. The present disclosure, however, provides an alternative configuration for the locking and cutting devices 50 and 56. FIG. 11 illustrates another exemplary embodiment where locking device 50 and cutting device 56 are combined into a single integrated device 84. Integrated device 84 includes a mounting structure 86 for mounting each of locking device 50' and cutting device 56'. Mounting structure 86 is a generally rectangular-shaped planar member having rectangular-shaped cut-outs 87 where movable pegs 60' are located. The peg 60' of cutting device 56' includes a blade 66', while the peg 60' of locking device 50' includes a gripping surface 68'. To actuate each peg 60', each peg 60' is coupled to cams 88 that are hingedly coupled to one another. To actuate cams 88, pull bars 90 having apertures 92 that cooperate with shape-memory alloy wires (not shown) are used. In this regard, upon application of a voltage to the shape memory alloy wires, the wires will contract and pull the pull bars 90 to straighten the cams 88, which will push pegs 60' in a direction out of cut-outs 87 to either cut or engage the sutures. Cams 88 are secured to pegs 60', mounting structure 86, and pull bars 90 using pins 94, 96, and 98. To ensure that cams 88 return to a non-straightened state that disengages the blade 66' or gripping surface 68' from the suture, an elastic member (not shown) may be looped around pins 96 and 98.

Figure 12:
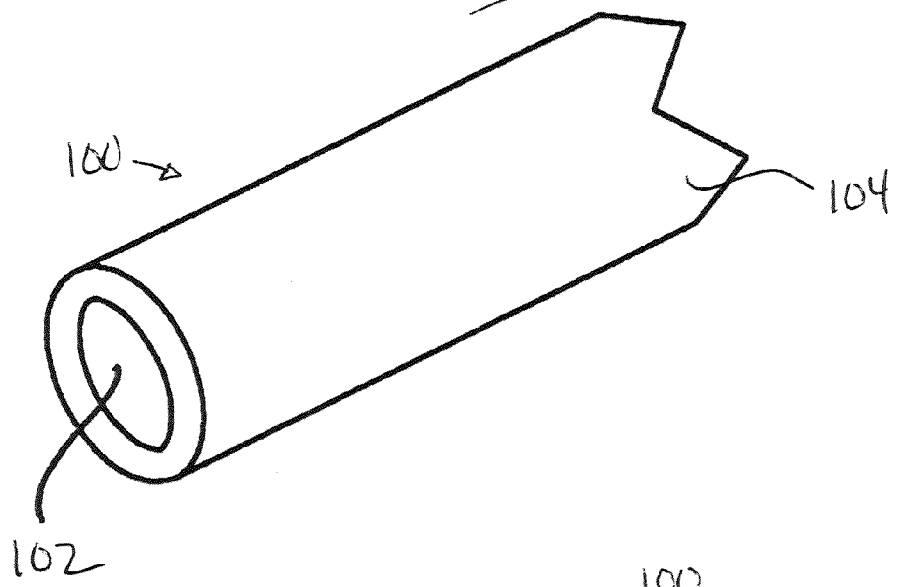
FIGS. 12-13 are various perspective view of a suture according to a principle of the present disclosure.
Figure 13:
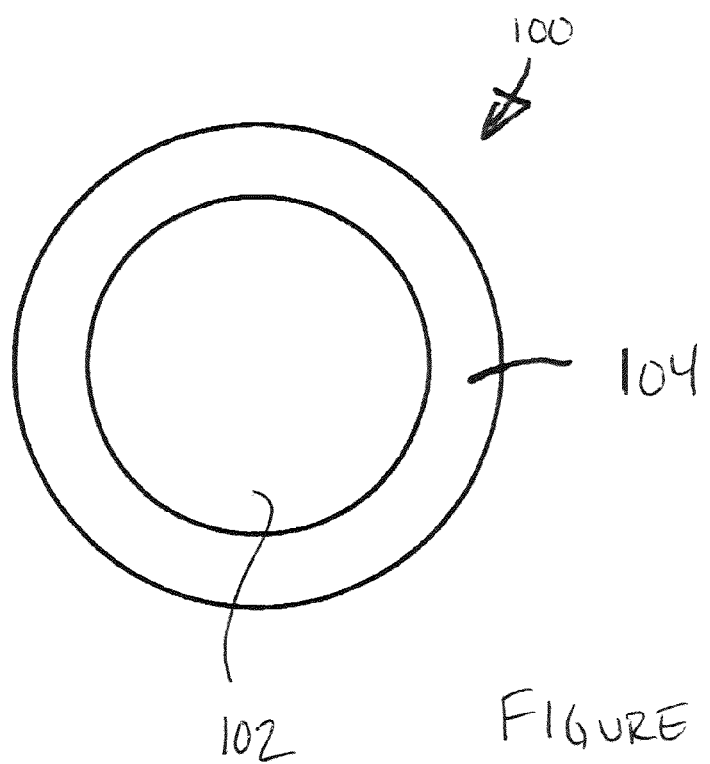

As noted above, heating element 54 is designed to fuse opposing ends of a suture together. To accomplish this, the suture 100 is a specially designed suture formed of at least a pair of materials. Specifically, referring to FIGS. 12-13, suture 100 includes a core material 102 and a sheath or coating material 104 that is extruded around the core material 102. The core material 102 can be formed of a material such as polyglycolic acid (PGA), while the coating 104 can be formed of a material such as polycaprolactone (PCL).

The PCL coating 104 has a melting temperature of about 60 C, and the melting temperature of the PGA core material 102 is about 230 C. Because of the extreme difference in melting temperatures, the PCL coating material 104 can be melted to fuse the opposing ends of the suture 100 without damaging the vessel being ligated and without melting the PGA core material 102. To ensure compatibility between the core material 102 and the coating material 104, various plasticizers such as polylactic acid (PLA) or poly-3-hydroxybuterate (P3HB) can be used to ensure adhesion between the core material 102 and the coating 104. Regardless, the core 102 may include a diameter in the range of 0.3 to 0.6 mm, while the coating may include a thickness ranging between 0.05 and 0.2 mm.

It should be understood, however, that the above-noted diameters and thicknesses can be adjusted without departing from the scope of the present application. Further, although the above-noted materials for core 102 and coating 104 are preferable, it should be understood that other materials are contemplated so long as coating 104 has a melting point that is less than core 102, and so long as the materials will dissolve after a predetermined period of time within the body.

Figure 14:
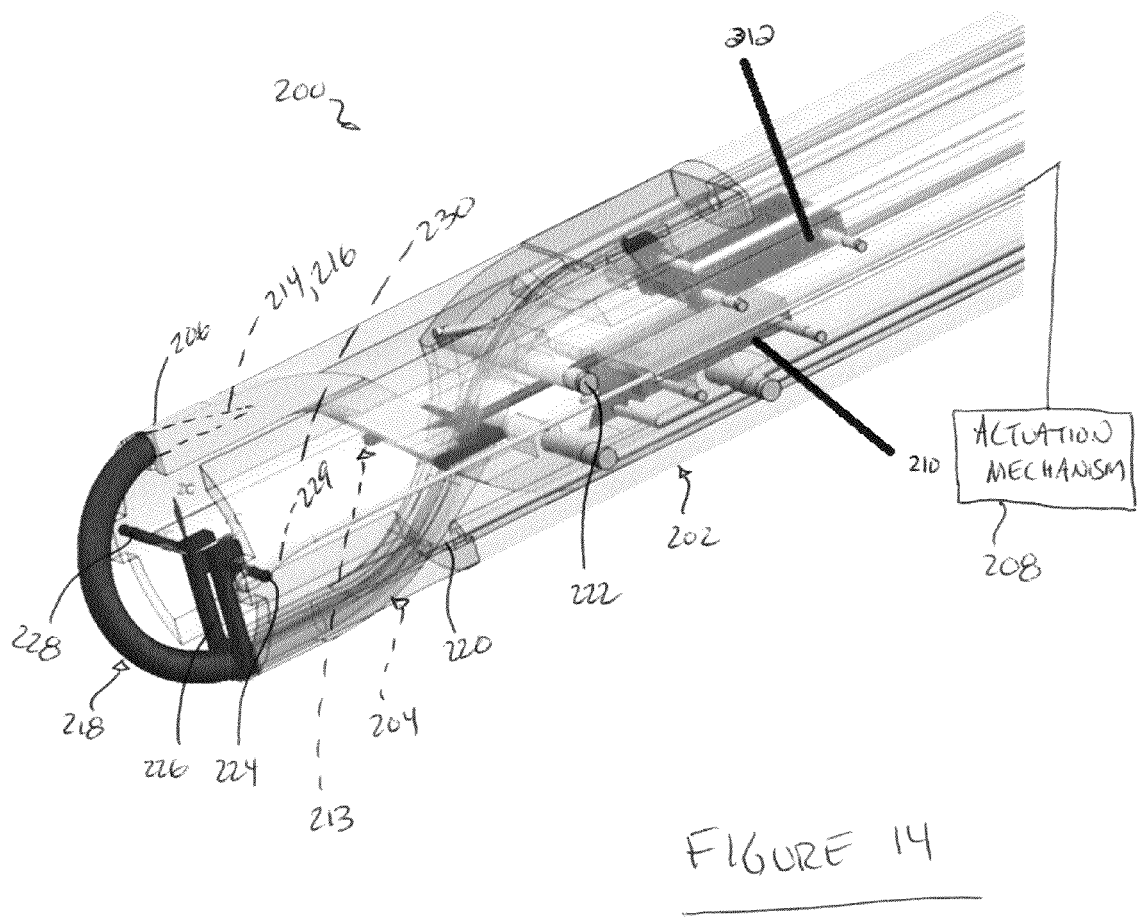
FIG. 14 is a perspective view of another suture device according to a principle of the present disclosure.
Figure 15:
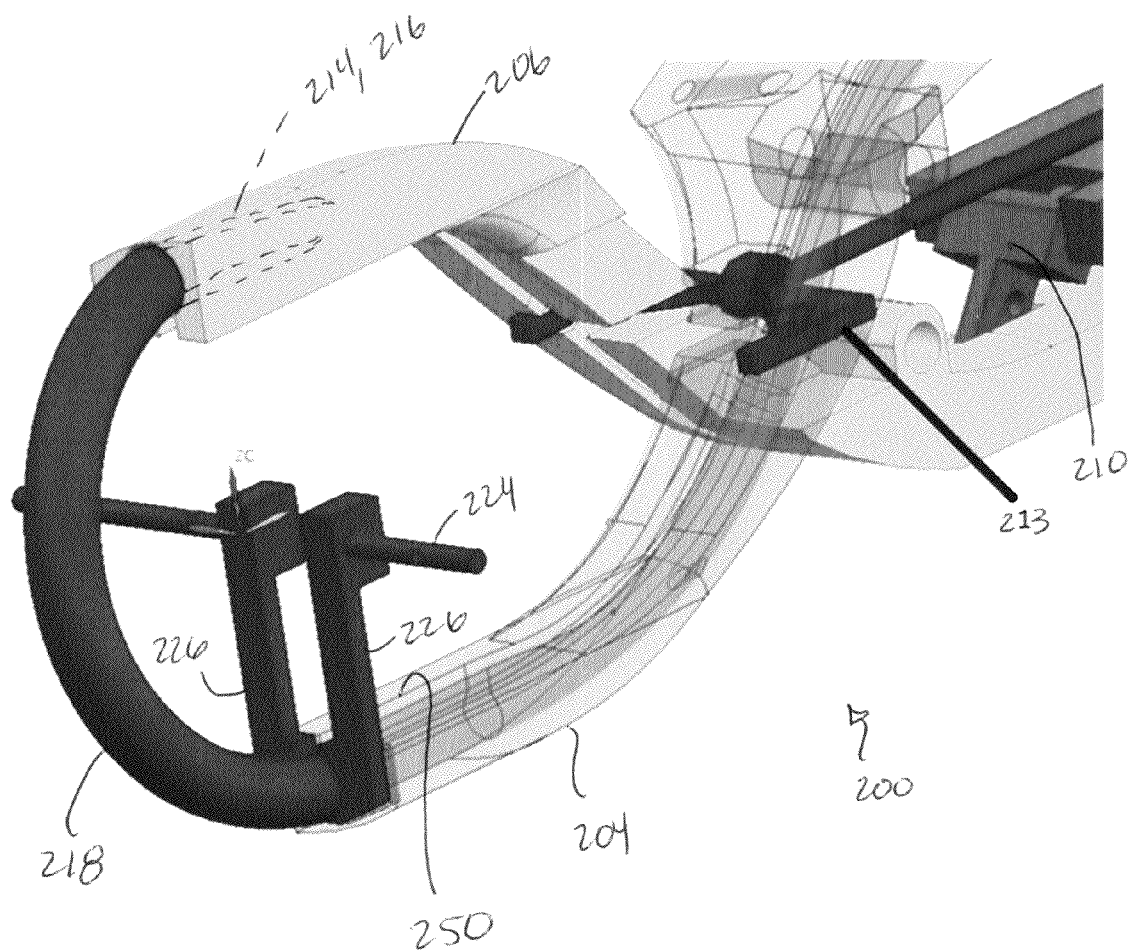
FIG. 15 is another perspective view of the suture device illustrated in FIG. 14, with a shaft thereof removed.

Now referring to FIGS. 14 and 15, another suture device 200 is illustrated. Suture device 200 is similar to suture device 10 in that suture device 200 includes an elongated shaft 202, an upper jaw 204, and a lower jaw 206 that can be mechanically or electrically activated using an actuation mechanism 208. Additionally, suture device 200 can include a locking mechanism 210, a cutting mechanism 212, and a heating element 213 that are similar to and function in the same manner as locking device 50, cutting device 56, and heating element 54 described above. The primary distinguishing feature between suture device 200 and suture device 10 is the additional feature of a hollow curved needle 214, and end 216 of which may be seen in phantom in lower jaw 206. The rest of the needle (not shown) is fixed to an interior (not shown) of curved sleeve 218. Rotation of sleeve 218 relative to shaft 202 allows needle 214 to retract from lower jaw 206, and then be advanced through tissue and/or a mesh material back into lower jaw 206 to pass the suture through the tissue, as will be described below.

To retract needle 214 from lower jaw 206, upper jaw 204 can first be moved to allow rotation of sleeve 218. To actuate upper jaw 204, upper jaw 204 is coupled to a wire 220 that may be mechanically or electrically actuated by actuation mechanism 208. When wire 220 is pulled in a direction away from sleeve 218, upper jaw 204 will be pivoted about pin 222 in a direction (downward direction in FIG. 14) away from sleeve 218. Then, sleeve 218 may be rotated about pin 224 that is unitary or at least integral with sleeve 218. More specifically, sleeve 218 includes a pair of arms 226 that are coupled to pin 224, which in turn is mated with apertures 228 formed in shaft 202.

To rotate sleeve 218 about pin 224, pin 224 is coupled to a first wire 229 that can be wrapped about pin 224. When first wire 228 is pulled in a direction away from sleeve 218, first wire 229 will rotate (e.g., in a counter-clockwise direction in FIG. 14) to rotate sleeve 218 away from lower jaw 206, which retracts needle 214 out of lower jaw 206. To advance needle 214 back into lower jaw 206, a second wire 230 is coupled to an opposite end of pin 224. Second wire 230 can be wrapped in a different direction around pin 224. As such, when second wire 230 is pulled in a direction away from sleeve 218, second wire 230 will rotate (e.g., in a clock-wise direction in FIG. 14) to rotate sleeve 218 towards lower jaw 206, which will advance needle 214 back into lower jaw 206.

As best shown in FIG. 15, it should be understood that upper and lower jaws 204 and 206 each include a channel 250 and 252, respectively, for carrying a suture such as suture 100. Furthermore, it should be understood that needle 214 is hollow and operable to carry suture 100 therethrough as well. In this manner, during use of device 200, upper jaw 204 can be actuated to allow sleeve 218 to rotate away from lower jaw 206 to retract needle 214 from lower jaw 206.

After being retracted from lower jaw 206, needle 214 can then be pierced through tissue and/or a mesh material that requires securing. After piercing the tissue and/or mesh, needle 214 can be re-engaged with lower jaw 206 through rotation of sleeve 218 back towards lower jaw 206. After re-engagement with lower jaw 206, upper jaw can be re-aligned with sleeve 218, and suture 100 can advanced through channel 250 formed in upper jaw 204, the hollow sleeve and needle 218 and 214, and into channel 252 of lower jaw 206 towards locking mechanism 210 where suture 100 can be secured. Then, after heating element 213 fuses opposing ends of suture 100, cutting mechanism 212 can cut suture 100 to complete the suturing procedure. Suture device 200 is then free to be used again at a different location, without removing suture device 200 from the patient's body if the device is inserted into the patient's body.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture device, comprising:
a shaft having an interior;
a pair of jaws disposed at a distal end of the shaft, at least one of the jaws being movable, and each of the jaws including a channel for carrying a suture; and
a heating device disposed in the interior of the shaft, and movable relative to the shaft and the pair of jaws,
wherein the heating device is operable to fuse opposing ends of the suture as it passes through each of the channels, the heating device is a planar member including a pair of wing-shaped guiding elements that terminate at a seat positioned between each of the wino-shaped guiding elements, each wing-shaped guiding element defining a U-shaped recess configured to catch and force the opposing ends of the suture from the channels of the each of the jaws into the seat.

2. The suture device of claim 1, further comprising a locking device for gripping an end of the suture.

3. The suture device of claim 2, further comprising a cutting device for cutting an opposing end of the suture.

4. The suture device of claim 3, wherein each of the locking device and cutting device are actuated by wires coupled to an actuation mechanism.

5. The suture device of claim 4, wherein the wires are formed from a shape-memory alloy.

6. The suture device of claim 1, wherein each of the jaws includes a slot configured to receive passage of the heating device.

7. The suture device of claim 1, wherein at least one of the jaws forms a hollow needle.

8. A suture device, comprising:
a hollow shaft;
a pair of jaws disposed at an end of the hollow shaft, at least one of the jaws being actuated by an actuation arm coupled to an actuation mechanism, and each of the jaws including a channel formed therein for carrying a suture;
a locking device disposed in the hollow shaft operable to grip an end of the suture;
a cutting device disposed in the hollow shaft operable to cut an opposing end of the suture; and
a heating device configured to remove the suture from the channels of the pair of jaws, and fuse the suture,
wherein the heating device is a planar member including a pair of wing-shaped guiding elements that terminate at a seat positioned between each of the wing-shaped guiding elements, each wing-shaped guiding element defining a U-shaped recess configured to catch and force opposing ends of the suture from the channels of the each of the jaws into the seat.

9. The suture device of claim 8, wherein each of the jaws includes a slot configured to receive passage of the heating device.

10. The suture device of claim 8, wherein each of the locking device and cutting device are actuated by wires coupled to an actuation mechanism.

11. The suture device of claim 10, wherein the wires are formed from a shape-memory alloy.

12. The suture device of claim 8, wherein at least one of the jaws forms a hollow needle.

* * * * *